United States Patent [19]
Plochocka et al.

[11] Patent Number: 6,048,522
[45] Date of Patent: Apr. 11, 2000

[54] CONTROLLED-RELEASE, DRUG-DELIVERY COMPOSITION

[75] Inventors: Krystyna Plochocka, Scotch Plains; Jui-Chang Chuang, Wayne; Jenn S. Shih, Paramus; Anil Menon, Bridgewater; Nadhamuni G. Nerella, Wayne, all of N.J.

[73] Assignee: ISP Investments Inc., Wilmington, Del.

[21] Appl. No.: 09/121,380

[22] Filed: Jul. 23, 1998

Related U.S. Application Data

[63] Continuation-in-part of application No. 08/988,121, Dec. 10, 1997.
[51] Int. Cl.⁷ .......................... A61K 9/113; A61K 31/74; A61K 31/79; A61K 31/695
[52] U.S. Cl. ..................... 424/78.24; 424/78.03; 424/70.12; 424/78.18; 424/78.24; 428/402.22; 526/194; 526/263; 526/264
[58] Field of Search ..................... 526/194, 263, 526/264; 424/78.03, 78.24, 78.18, 70.12; 428/402.22

[56] References Cited

U.S. PATENT DOCUMENTS

| | | | |
|---|---|---|---|
| 5,130,121 | 7/1992 | Kopolow | 424/47 |
| 5,156,914 | 10/1992 | Shih | 428/402.22 |
| 5,189,102 | 2/1993 | Tsubuko | 525/112 |

*Primary Examiner*—Fred Zitomer
*Attorney, Agent, or Firm*—Dr. Walter Katz; William J. Davis; Marilyn J. Maue

[57] ABSTRACT

A controlled-release, drug-delivery, emulsion composition for topical application comprising (a) the reaction product of the non-aqueous, heterogeneous polymerization of a reaction mixture of about 5–70%, preferably 10–30%, by weight, of a vinyl monomer in an oil as solvent, and a free radical initiator, optionally in the presence of a crosslinking agent and/or a surfactant, wherein the oil solvent is present in an amount sufficient to keep the resultant polymer in a stirrable state throughout the polymerization, (b) water, (c) a surfactant and (d) a pharmaceutical medicament.

16 Claims, 2 Drawing Sheets

CONTROLLED-RELEASE, DRUG-DELIVERY COMPOSITION

CROSS-REFERENCE TO RELATED U.S. PATENT APPLICATION

This application is a continuation-in-part of Ser. No. 08/988,121, filed Dec. 10, 1997, assigned to the same assignee as herein.

BACKGROUND OF THE INVENTION

1. Field of the Invention

This invention relates to controlled-release, drug-delivery systems for effecting the desired controlled-release of pharmaceutical medicaments in a topical application.

2. Description of the Prior Art

In the pharmaceutical industry much work has been devoted during recent years to improving the effectiveness, safety and practicality of administered drugs. Accordingly, this invention is specifically directed toward the goal of prolonging the release of a topically applied drug over a period of several hours. Such a prolonged release has the following advantages: peak blood levels of the drug which sometimes represent toxic levels are avoided since not all the drug is released at the same time; secondly, drug concentrations in the blood are maintained for a longer time within the therapeutic range, thereby increasing the overall effectiveness of the drug and reducing the overall dose-size necessary for treatment; thirdly, drugs which would have to be taken in conventional form several times daily for the treatment of chronic diseases, can be topically applied in once or twice-a-day dose forms, which are safer and more convenient for the patient.

Accordingly, it is an object of this invention to provide a controlled-release, drug-delivery composition for topical application comprising an effective amount of a pharmaceutical medicament in an emulsion containing polymer.

Another object herein is to provide a controlled-release, topically appliable drug-delivery, emulsion composition which includes the polymeric reaction product of a non-aqueous, heterogeneous polymerization process for making vinyl polymers using an oil solvent.

These and other objects and features of the invention will be made apparent from the following description of the invention.

IN THE DRAWING

The FIGS. 1 and 2 are graphical representation of % drug released vs. time for typical compositions of the invention.

SUMMARY OF THE INVENTION

What is described herein is a controlled-release, drug-delivery, emulsion composition for topical application comprising (a) the reaction product of, by weight, about 5–70%, preferably 10–30% of a vinyl monomer in an oil as solvent, and a free radical initiator, optionally in the presence of a crosslinking agent and/or a surfactant, wherein the oil solvent is present in an amount sufficient to keep the resultant polymer in a stirrable state throughout the polymerization, (b) water, (c) a surfactant and (d) a pharmaceutical medicament.

DETAILED DESCRIPTION OF THE INVENTION

Figure 1:
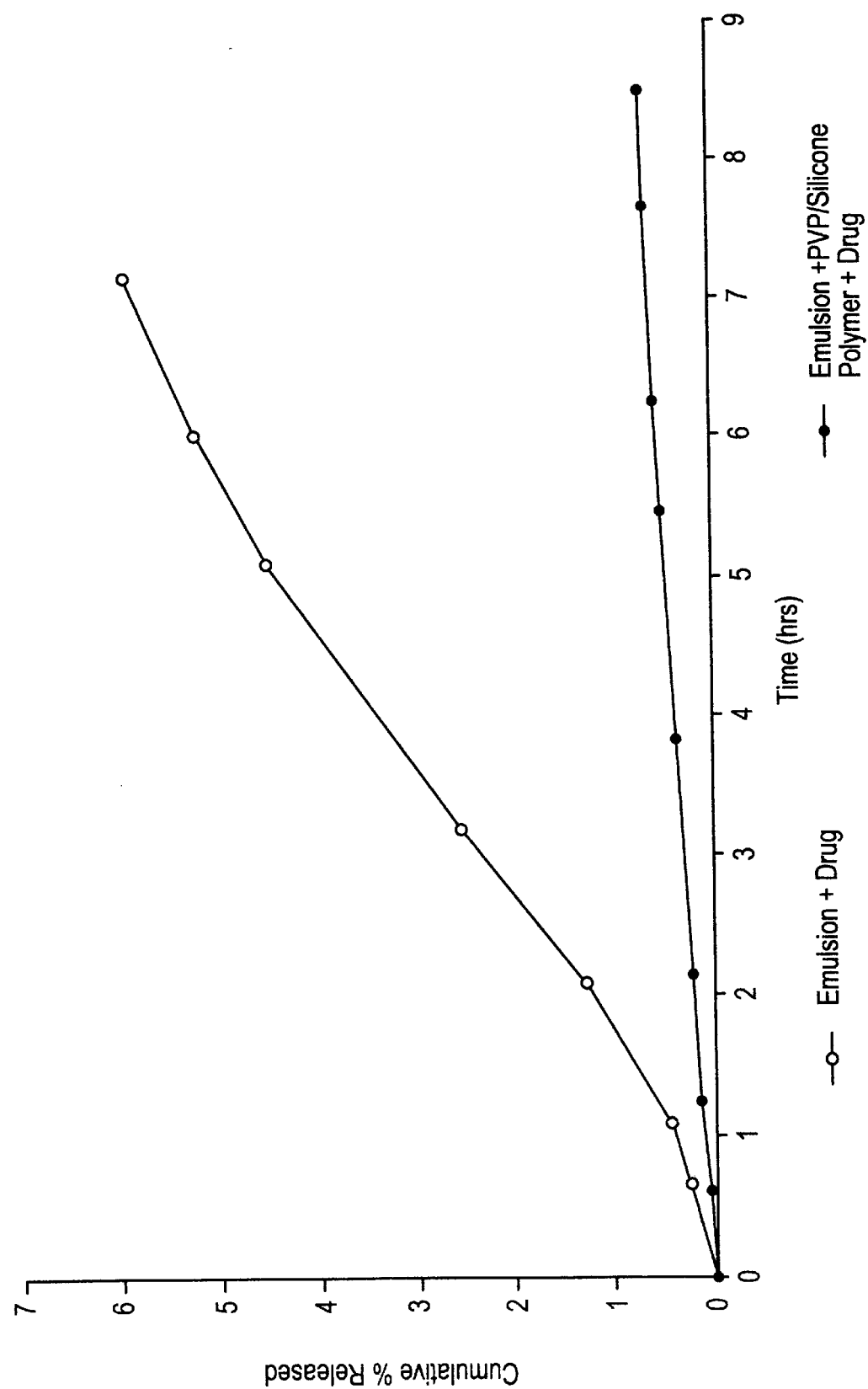

The unique properties of many oils make it desirable to include them in aqueous-based compositions. For example, cosmetically and pharmaceutically-acceptable materials such as silicone oils, fluids and gums, mineral oils, and water-insoluble organic esters such as isopropyl palmitate and isopropyl myristate.

In this invention, vinyl polymers useful in controlled-release, topically appliable drug-delivery compositions are prepared in a non-aqueous, heterogeneous polymerization process using an oil as a solvent for the monomer during the polymerization reaction. The oil solvent also acts as a medium to keep the polymer product in a stirrable state throughout the polymerization. The reaction product is a slurry of the vinyl polymer in oil. If desired, the reaction product may be filtered to provide the vinyl polymer as a powder swollen with oil. Thereafter, the reaction product itself, or the polymer powder swollen with oil, may be homogenized with water to form a uniform liquid emulsion or gel which is directly useful in the pharmaceutical composition.

Generally about 5–70%, preferably 10–30%, by weight, of the vinyl monomer reactant is used in the process, and about 30–95% of the oil is included for the solvent and medium functions in the process.

Suitable silicone oils or fluids for use in the invention may be selected from non-volatile silicones, such as polyalkyl siloxanes, polyaryl siloxanes, polyalkylaryl siloxanes and polyether siloxane copolymers; and volatile silicones such as cyclomethicones also may be used.

Non-volatile polyalkylsiloxanes thus include, for example, polydimethylsiloxanes (Dimethicone) with viscosities ranging from about 5 to about 600,000 centistokes (cS) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued Jul. 20, 1970. Preferably, the viscosity of these siloxanes selected have a viscosity of about 100 to about 100,000 cS, and most preferably, a viscosity of up to about 15,000 cS.

Suitable non-volatile polyalkylaryl siloxanes include, for example, poly(methylphenyl siloxane having viscosities of about 15 to 65 cS at 25° C. These siloxanes are available, for example, from the General Electric as SF 1075 methylphenyl fluid or from Dow Corning as 556 Cosmetic Grade Fluid. Additionally, poly(dimethylsiloxane)-(diphenylsiloxane) copolymers having a viscosity in the range of about 10 to 100,000 cS at 25° C. are useful.

These and other suitable silicones are disclosed in U.S. Pat. Nos. 2,826,551, 3,964,500 and 4,364,837.

Other suitable oils for use herein include pharmaceutically-acceptable materials such as light and heavy mineral oils, and water-insoluble organic esters such as isopropyl palmitate and isopropyl myristate.

The polymerization process is carried out with a free radical initiator present in the polymerization reaction mixture. The reaction product thus includes the vinyl polymer corresponding to the vinyl monomer or monomers selected. Suitable free radical initiators are diacetyl peroxide, dibenzoyl peroxide, dilauroyl peroxide, t-butyl peroxypivalate, t-butyl peroctoate, t-amyl peroxypivalate, di-(4-t-butylcyclohexyl) peroxydicarbonate, 2,2'-azo-bis (isobutyronitrile), 2,2'-azo-bis(2,4-dimethyl-valeronitrile), or 1,1'-azo-bis(cyanocyclohexane), and mixtures thereof.

A crosslinked vinyl polymer may be obtained in the process when the optional crosslinking agent is included in the reaction mixture. Suitably, the crosslinking agent is present in an amount of about 0.1–10 wt. %, preferably 0.3–2%, based on the amount of vinyl monomer present. In the presence of such a crosslinking agent, the vinyl monomer will form the corresponding crosslinked vinyl polymer, which, upon homogenization with water, will provide a uniform liquid gel product.

In the practice of the present invention, the oil solvent is charged into a reactor, under agitation, and in a nitrogen atmosphere, and heated to about 40°–150° C., preferably about 65° C. Then the free radical initiator is added. Thereafter the vinyl monomer is added continuously over a period of about 1–12 hours, preferably about 3–6 hours. Preferably, the vinyl monomer and optional crosslinking agent are fed into the reactor at a rate such that substantially no free monomer is present during the polymerization.

After polymerization is complete, the polymer is obtained as a slurry in oil. The slurry can be used as is or filtered to remove excess oil where the product consists of solid polymer with significant amount of absorbed oil. Both slurry and filtered polymers are useful in pharmaceutical formulations.

Suitable vinyl monomers include, but are not limited to, N-vinylamides and N-vinyllactams, such as N-vinylpyrrolidone, N-vinylcaprolactam and N-vinylformamide, and optinally with comonomers such as vinyl acetate, acrylic acid, methacrylic acid, acrylamide, methacrylamide, an alkyl (meth)acrylate, an N-alkyl (meth) acrylamide, a hydroxyalkyl (meth)acrylate and a hydroxyalkyl (meth)acrylamide, and a N,N-dialkylaminoalkyl (meth)acrylate wherein alkyl is independently a $C_1$ to $C_{20}$ alkyl group and N,N-dialkylaminoalkyl methacrylamide (alkyl being as defined before), and their quaternary derivatives; and mixtures thereof.

Suitable crosslinking agents include, but are not limited to, diallylimidazolidone, divinyl ether of diethylene glycol, pentaerythritol triallyl ether (PETA); triallyl-1,3,5-triazine-2,4,6-(1H,3H,5H)trione (TATT), ethylene glycol diacrylate, 2,4,6-triallyloxy-1,3,5-triazine; N-vinyl-3-(E)-ethylidene-pyrrolidone (EVP), 1,7-octadiene, 1,9-decadiene, divinyl benzene, methylene-bis(methacrylamide), methylene-bis (acrylamide), N,N-divinylimidazolidone, ethylidene-bis(N-vinylpyrrolidone) (EBVP), hexaallyl sucrose, or bis(N,N-acrylamide).

Another optional component of the reaction mixture is a surfactant. The presence of a surfactant will function to effectively stabilize the desired emulsion and gel products. Generally, an oil soluble surfactant is present in the reaction mixture and a water soluble surfactant during the water homogenization, in an amount of about 0.5–10%, preferably 1–5%, based on oil present. Suitable oil soluble surfactants useful for polymerization include, but are not limited to, cetyl dimethicone copolyol (Abil® EM-90, product of Goldschmidt Chemical Corp.); Span® 80 (ICI) and Dow Corning 3225 silicone.

The products made herein may be easily converted into emulsions or emulsified hydrogels which contain the polymer (linear or crosslinked) in the aqueous phase. The oil phase consists of the oil used during polymerization. The emulsions can be a water-in-oil (w/o), oil-in-water (o/w), or mixed type (w/o/w). When the polymer is crosslinked, the aqueous phase has attributes of a swollen crosslinked hydrogel. The hydrogel phase can be either dispersed in oil as fine gel particles (w/o), or the oil droplets can be dispersed in a continuous hydrogel phase (o/w).

The selected ratios of oil-to-water in such emulsions and emulsified hydrogels are predetermined by the desired use compositions; these can be adjusted within a broad range. Typically, oil-to-water ratios reside in the range of about 30:70 to about 10:90 by volume in the case of o/w emulsions and emulsified hydrogels. In corresponding w/o systems, the ratios of oil-to-water are suitably in the range of about 90:10 to about 30:70 by volume. Typically, when there is a need for a significant amount of oil in the final emulsion, the reaction product, that is, the slurry of polymer in oil, is directly converted into an emulsion or an emulsified hydrogel by addition of a calculated amount of water. When, however, the ratio of oil-to-water in the emulsion is desired to be low, the emulsion is made using the filtered reaction product that consists of polymer powder swollen with the absorbed oil.

When an o/w system is desired, the reaction product is gradually added to water, whereas when a w/o system is desired, water is added gradually to the reaction product, with appropriate rapid agitation or homogenization. Suitable surfactants should be added to these systems, such as, for example, Tween® 20, 21, 40, 61 (ICI) or Igepal® CO-630 (product of Rhone-Poulenc), for o/w emulsions and emulsified hydrogels; and Span® 60, 65, 80, 85 (ICI) or Dow Corning® 3225C formulation aid for w/o systems. The surfactant added optionally to the polymerization reaction mixture also may be sufficient to form the desired emulsion or emulsified hydrogel.

The invention will now be described in further detail with reference to the following working examples

EXAMPLE 1

106.25 g of poly(dimethylsiloxane) silicone oil (Dow Corning 200® Fluid), having a Brookfield viscosity of 130 cS, was charged into a 1-liter glass resin kettle and heated to 65° C., while sparging with nitrogen. Then 0.05 g of t-butyl peroxypivalate (Lupersol® 11, 75% active, Elf Atochem), was added. Thereafter 18.75 g of N-vinylpyrrolidone (VP) monomer was continuously fed into the reactor over a period of 3 hours. Then a booster shot of 0.05 g Lupersol® 11 was added and the reaction was continued for another 2 hours. Still another booster of 0.05 g Lupersol® 11 was added and the reaction was continued for another 1 hour. The reaction mixture changed from a transparent oil into a white slurry. Then the slurry was filtered to yield 62 g of a white, waxy powder which was swollen with silicone oil. A sample of 10 g of the powder then was extracted with hexane and the extracted solid was dried under vacuum. A free-flowing PVP powder was obtained which weighed 2.5 g. Accordingly, the filtered polymer before extraction contained 75% of silicone oil. Its relative viscosity (1% in water) evaluated using the extracted sample was 1.71 at 25° C.

EXAMPLE 2

The process of Example 1 was carried out using 360 g of the silicone oil, 36 g VP and 0.3 g Lupersol® 11, which was added in three equal portions. The reaction product was filtered yielding 140 g of a white, oily PVP polymer powder containing 75% of silicone oil.

EXAMPLE 3

Into a 1-liter, 4-necked resin kettle, fitted with an anchor agitator, a nitrogen purge adaptor, a thermometer, two subsurface feeding tubes connected with two feeding pumps, and a reflux condenser, 400 g of 5 cS silicone oil was charged. Nitrogen purging was started and continued throughout the reaction. Agitation at 200 rpm was carried out throughout the process. The reactants were heated from ambient temperature to 65° C. in 20 minutes, and held at 65°

C. for 30 minutes. Then 260 microliter of t-butyl peroxypivalate (Luperso® 11) was charged and 200 g of N-vinylpyrrolidone was charged in 6 hours while holding the temperature at 65° C. The reaction was carried out at 65° C. for a half-hour. The reaction mixture then was transferred to a 2-liter high pressure reactor and 1 g of 2,5-dimethyl-2,5-bis(t-butylperoxy)hexane (Lupersol® 101) was charged into the reactor. Then the reactor was sealed and heated to 120° C. and held for 8 hours. The reaction product then was cooled to room temperature.

EXAMPLE 4

The process of Example 3 was carried out using a monomer mixture of 60 g of N-vinylpyrrolidone (VP), 20 g of lauryl methacrylate and 20 g of acrylic acid separately over a period of 3 hours in place of vinylpyrrolidone alone. The reaction product was a terpolymer of VP/lauryl methacrylate/acrylic acid (60/20/20) in silicone oil.

EXAMPLE 5

The process of Example 3 was carried out using a mixture of 400 g of Carnation® light mineral oil solvent and 5 g of cetyl dimethicone copolyol (Abil® EM-90) surfactant in place of silicone oil solvent alone. The reaction product was polyvinylpyrrolidone in mineral oil solvent and cetyl dimethicone copolyol surfactant.

EXAMPLE 6

The process of Example 3 was carried out by using a monomer mixture of 60 g of vinylpyrrolidone, 20 g of lauryl methacrylate and 20 g of acrylic acid, a solvent surfactant mixture of 400 g of light mineral oil and 5 g of cetyl dimethicone copolyol (Abil® EM-90). The reaction product was a terpolymer of VP/lauryl methacrylate/acrylic acid (60/20/20) in mineral oil with surfactant.

EXAMPLE 7

The process of Example 3 was carried out by pumping a mixture of 200 g of N-vinylpyrrolidone monomer and 0.90 g of pentaerythriol triallyl ether as crosslinker and 260 microliter of Lupersol® 11 initiator in 6 hours. The reaction product was crosslinked polyvinylpyrrolidone in silicone oil.

EXAMPLE 8

The process of Example 3 was carried out using added 5 g of cetyl dimethicone copolyol (Abil® EM-90) surfactant. The reaction product was polyvinylpyrrolidone in silicone oil with surfactant present.

EXAMPLE 9

The process of Example 4 was carried out with 5 g of cetyl dimethicone copolyol (Abil® EM-90) present. The reaction product was VP/lauryl methacrylate/acrylic acid (60/20/20) terpolymer in silicone oil with surfactant present.

EXAMPLE 10

The process of Example 4 was carried out in Carnation® light mineral oil with 5 g of cetyl dimethicone copolyol (Abil® EM-90) surfactant and 0.45 g of pentaerythriol triallyl ether crosslinker present. The reaction product was crosslinked terpolymer of VP/lauryl methacrylate/acrylic acid (60/20/20) as above in mineral oil with surfactant present.

EXAMPLE 11

A mixture of 52.5 g of the filtered reaction product of Example 2 with 60 g of its filtrate added and 33 g of Dow Corning® 3225C silicone as surfactant were charged into a 1-liter vessel and homogenized to provide a uniform slurry. Homogenization was continued while 157 g of water was added dropwise over 30 min. Homogenization was continued for an additional 10 min. A uniform, white liquid emulsion was obtained having a Brookfield viscosity of 270 cPs (Spindle # 4, 20 rpm). The emulsion remained stable upon standing for 2 months; and was dilutable with silicone oil, indicating it was a water-in-oil (w/o) emulsion.

EXAMPLE 12

A 1-liter resin kettle was charged with 205 g of Dow Corning 200® Fluid silicone oil, sparged with nitrogen and heated to 65° C. Then 0.25 g of Lupersol® 11 was added. Thereafter, a mixture of 36 g of N-vinylpyrrolidone, 0.16 g of triallyl-1,3,5-triazine-2,4,6-trione (TATT) as crosslinker and 0.72 g of Span® 80 surfactant was added over 6 hours, with two additions of 0.25 g each of Lupersol® 11 after 3 and 6 hours. The reaction was continued for an additional 1 hour whereafter the reaction slurry was cooled and filtered to yield 123 g of a waxy precipitate containing about 75% silicone oil. After extraction of the silicone oil from the precipitate, the dried solid was introduced into water (a 5% by wt. solution). A gel product was obtained having a Brookfield viscosity of 2410 cps at 20 rpm.

EXAMPLE 13

The process of Example 12 was repeated using Dow Corning® 3225C as a surfactant instead of Span® 80. The product was crosslinked PVP containing about 73% silicone oil. Then 1 g of the extracted, dried polymer powder was added to 100 g water. After 24 hours at room temperature, the crosslinked polymer powder swelled into 22 ml of a gel phase.

EXAMPLE 14

A mixture of 52.5 g of the crosslinked PVP of Example 13 was homogenized with 60 g of its filtrate added and 33 g of Dow Corning® 3225C silicone surfactant. Then, continuing homogenization, 157 g of water was added dropwise over 45 minutes. Homogenization was continued for about 20 minutes using an ice bath to cool the resulting emulsion. A smooth, uniform emulsion was obtained which was similar to cosmetic face cream in consistency. Dilution with silicone oil did not change its appearance, indicating a water-in-oil (w/o) emulsion, containing crosslinked polymer in aqueous phase. The emulsion had a Brookfield viscosity of 270 cps at 20 rpm; its viscosity and appearance remained unchanged for 2 months at room temperature.

EXAMPLE 15

28 g of the filtered crosslinked PVP of Example 13 was added gradually to 133 g of an aqueous 0.5% solution of Igepal® CO-630 surfactant, under homogenization. A uniform, slightly hazy mixture was obtained to which there was added, dropwise, over 15 minutes, 39 g of Dow Corning 200® Fluid silicone oil. Homogenization was continued for an additional 30 minutes using an ice bath to cool the emulsion. A milky, viscous emulsion was obtained, which could be diluted with water, indicating an o/w emulsion. The Brookfield viscosity was 2490 cps at 20 rpm.

EXAMPLE 16

A 1-liter resin kettle was charged with 500 g of Dow Corning 200® Fluid silicone oil. The oil was sparged with nitrogen, heated to 65° C. and maintained under a nitrogen blanket. Then 10 g of silicone surfactant DC 3225C (Dow Corning) and 0.25 g Lupersol® 11 (Elf Atochem) initiator were added, and, over 6 hours, a blend of 55.75 g of N-vinylpyrrolidone, 7.72 g of Ageflex® FA-1 (N,N-dimethylaminoethyl methacrylate, a product of CPS Chemical Co.) and 19.14 g of Ageflex® FM-1Q80DMS (N,N-diethylaminoethyl methacrylate dimethyl sulfate quaternary, 80% active, a product of CPS Chemical Co.) was admitted. Hourly during this feeding of monomers, there was added 0.25 g Lupersol® 11, i.e. a total of five initiator boosters. After feeding was completed, the temperature was maintained for 2 hours. The reaction was cooled to yield a white slurry of the resultant polymer in silicone oil. The slurry was filtered to yield 197 g of a waxy powder containing 80.7 g of N-vinylpyrrolidone/N,N-dimethylamino-ethyl methacrylate/N,N-dimethylaminoethyl methacrylate diethyl sulfate quaternary terpolymer, as determined by extraction with hexane, and the remainder was silicone oil.

Preparation of a Drug-Containing Composition The Active Ingredient (Drug)

Any of the drugs used to treat the body can be incorporated as the active agent in the polymeric carrier of this invention. "Drug" is used herein in its broadest: sense as including any composition of matter that will produce a pharmacological or biological response.

Suitable drugs for use in therapy according to this invention include, without limitations, those listed in U.S. Pat. No. 3,732,865 (columns 10 and 11).

Other drugs having the same or different physiological activity as those recited above can be employed in carriers within the scope of the present invention. Suitable mixtures of drugs can, of course, be dispensed with equal facility as with single component systems.

Drugs can be in various forms, such as uncharged molecules, components of molecular complexes, or nonirritating pharmacologically acceptable salts, e.g. the hydrochloride, hydrobromide, sulphate, phosphate, nitrate, borate, acetate, maleate, tartrate, salicylate, etc. For acidic drugs, salts of metals, amines, or organic cations (e.g. quaternary ammonium) can be employed. Furthermore, simple derivatives of the drugs (such as ethers, esters, amides, etc.) can be employed.

The amount of drug incorporated in the carrier varies widely depending on the particular drug, the desired therapeutic effect, and the time span for which it takes the drug to be released. Since a variety of carriers in a variety of sizes and shapes are intended to provide complete dosage regimen for therapy for a variety of maladies, there is no critical upper limit on the amount of drug incorporated in the carrier. The lower limit, too, will depend on the activity of the drug and the span of its release from the carrier. Thus, it is not practical to define a range for the therapeutically effective amount of drug to be released by the carrier.

Preferred drugs to be incorporated according to the present invention are those which can be topically aplied and are designed for long-term treatment so that multiple daily doses can be avoided. For example, smooth muscle relaxants, e.g. analgesics, e.g. acetylsalicyclic acid, phenylbutazone or methadone; antibiotics, e.g. metronidazole; antihistamines, e.g. tripelennamine; antiinfectives, e.g. trimethoprim; antiparasitics, e.g. nifurimox; corticoids, e.g. dexamethasone; cytostatics, e.g. floxuridine; neuroleptics, e.g. reserpine or thioridazine; psychoanaleptics, e.g. methylpenidate; uricosutics, e.g. sulfinpyrazone.

Among the most preferred drugs are metronidazole; diclofenac-sodium (VOLTRAREN), baclofen (LIORESAL), metropolol.HCl (LOPRESSOR); calcium channel blockers, such as Nifedipine and Verapamil, diisopyramide, ketoconazole, nystatin, clobidazole and erythromycin.

Controlled-Release Tests FIG. 1

Metronidazole was used as a model drug in this study. Metronidazole is an antibacterial whose preparations are indicated for topical application of inflammatory capules and custules.

The primary emulsion was prepared by mixing silicone oil-344 (26.2%) and silicone aid-3225C (32.3%) for 5 minutes and then adding Span® 80 (10.8%) to the mixture. Then distilled water (30.7%) was gradually added with constant agitation. The primary emulsion was stable for 3 weeks.

30 g of the primary emulsion was used for preparation of the following formulations:

○ Primary emulsion+drug (1 g) [pH 7.14]

● Primary emulsion+filtered PVP/silicone polymer (composition of Example 7) (9 g)+drug (1 g) [pH 5.56].

The release studies were carried out in diffusion cells, which simulate a topically applied system. The rate limiting membrane was cellulosic (MW 1000). The membrane was soaked overnight in distilled water. The prepared cells were overturned onto a beaker-placed on a magnetic stirrer containing 125–135 ml of distilled water and periodic samples withdrawn over 7–8 hours for drug release analysis. The results are shown in FIG. 1.

The invention emulsion formulation (●) is seen to retard the release of the drug more substantially than the emulsion itself (○).

FIG. 2

Diisopyramide phosphate, a freely water soluble antiarrhythmic drug was chosen as another model compound. The invention test composition was formulated by mixing 10 g of the drug dissolved in 42 g of water under continuous agitation and 48 g of the moderately crosslinked PVP/silicone oil product of Example 7.

The drug release studies were carried out using an Enhancer™ cell used in conjunction with a USP paddle type dissolution apparatus which allowed the study of drug release from topical dosage forms. The enhancer cells were packed with 0.2 g of the test emulsion formulation. A cellulosic membrane was used as a barrier membrane between the emulsion compartment of the cell and the dissolution medium. Then the enhancer cells packed with drug loaded emulsion were placed in USP paddle type dissolution apparatus. Dissolution paddles were rotated at 50 rpm. The dissolution medium was water. Samples were periodically withdrawn and % drug released was estimated based on a UV calibration curve.

Figure 2:
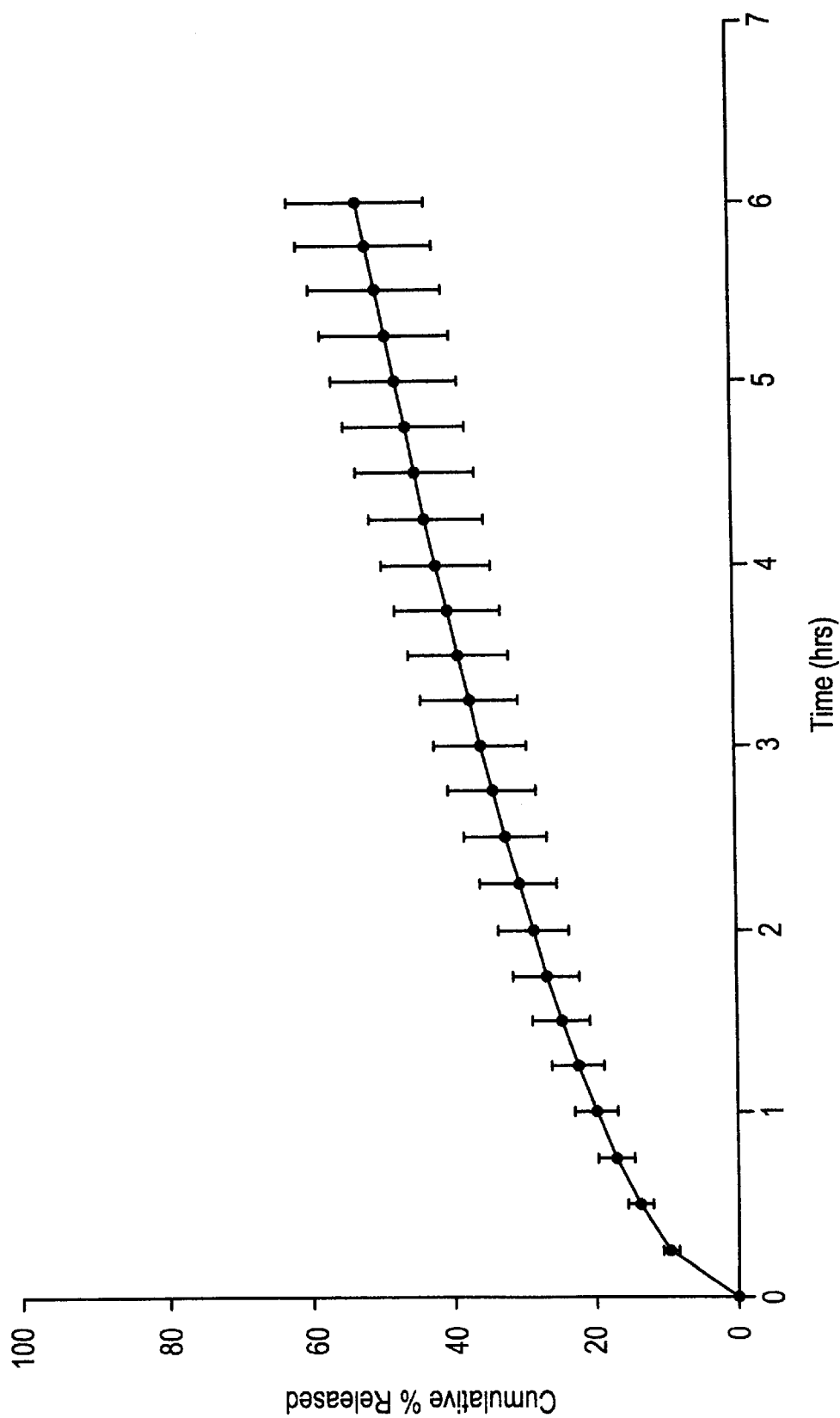

FIG. 2 shows the cumulative release profile of the diisopyramide phosphate drug from the emulsion composition. Over a period of 6 hours only 60% of the drug was released which indicated a controlled release pattern.

While the invention has been described with particular reference to certain embodiments thereof, it will be understood that changes and modifications may be made which are within the skill of the art. Accordingly, it is intended to be bound only by the following claims, in which:

What is claimed is:

1. A controlled-release drug-delivery, emulsion composition suitable for topical application comprising: (a) the reaction product of the non-aqueous, heterogeneous polymerization of a reaction mixture comprising, by weight, about 5–70% of a vinyl monomer in about 30–95% of an oil as solvent, wherein the oil is selected from the group consisting of a silicone oil, a mineral oil or a water-insoluble organic ester and a free radical initiator, optionally in the presence of a crosslinking agent and/or an oil soluble surfactant, with agitation, under an inert gas, at about 40–150° C. wherein the oil is present in an amount sufficient to keep the resultant vinyl polymer in a stirrable state until the end of the polymerization, (b) water to form an oil-in-water, a water-in-oil or a water-in-oil-in-water emulsion or gel, in a volume ratio of oil-in-water of 30:70 to 10:90, or water-in-oil of 90:10 to 30:70, (c) an added surfactant, if a suitable surfactant was not present during polymerization and (d) a pharmaceutical medicament.

2. A composition according to claim 1 wherein the reaction mixture includes about 0.1–10 wt. % of a crosslinking agent, based on the amount of vinyl monomer present.

3. A composition according to claim 2 wherein said crosslinking agent is present in an amount of 0.3–2%.

4. A composition according to claim 1 wherein the vinyl monomer is a N-vinylamide or N-vinyllactam selected from N-vinylpyrrolidone, N-vinylcaprolactam, and N-vinylformamide, optionally with a comonomer selected from vinyl acetate, acrylic acid, methacrylic acid, acrylamide, methacrylamide, an alkyl (meth)acrylate, an alkyl (meth)acrylamide, a hydroxyalkyl (meth)acrylate and a hydroxyalkyl (meth)acrylamide; and a N,N-dialkylaminoalkyl (meth)acrylate and a N,N-dialkylaminoalkyl methacrylamide wherein alkyl is independently a $C_1$ to $C_{20}$ alkyl group, and N-quaternary derivatives thereof; and mixtures thereof.

5. A composition according to claim 4 wherein the vinyl monomer is N-vinylpyrrolidone.

6. A composition according to claim 4 wherein the vinyl monomer is a mixture of N-vinylpyrrolidone, lauryl methacrylate and acrylic acid.

7. A composition according to claim 4 wherein the vinyl monomer is a mixture of N-vinylpyrrolidone, N,N-dimethylaminoethyl methacrylate and N,N-dimethylaminoethyl methacrylate dimethyl sulfate quaternary.

8. A composition according to claim 1 wherein the crosslinking agent is diallylimidazolidone, divinyl ether of diethylene glycol, pentaerythritol triallyl ether (PETA); triallyl-1,3,5-triazine-2,4,6-(1H,3H,5H)trione (TATT), ethylene glycol diacrylate, 2,4,6-triallyloxy-1,3,5-triazine; N-vinyl-3-(E)-ethylidene-pyrrolidone (EVP), 1,7-octadiene, 1,9-decadiene, divinyl benzene, methylene-bis(methacrylamide), methylene-bis(acrylamide), N,N-divinylimidazolidone, ethylidene-bis(N-vinylpyrrolidone) (EBVP), hexaallyl sucrose, or bis(N,N-acrylamide).

9. A composition according to claim 8 wherein the vinyl monomer is N-vinylpyrrolidone.

10. A composition according to claim 8 wherein the vinyl monomer is a mixture of N-vinylpyrrolidone, lauryl methacrylate and acrylic acid.

11. A composition according to claim 8 wherein the vinyl monomer is a mixture of N-vinylpyrrolidone, N,N-dimethylaminoethyl methacrylate and N,N-dimethylaminoethyl methacrylate dimethylsulfate quaternary.

12. A composition according to claim 1 wherein the vinyl monomer, and optional crosslinking agent, are fed into the reactor charged with oil and free radical initiator continuously over a period of about 1–12 hours at a rate such that substantially no free monomer is present during the polymerization.

13. A composition according to claim 1 wherein the free radical initiator is diacetyl peroxide, dibenzoyl peroxide, dilauroyl peroxide, t-butyl peroxypivalate, t-amyl peroxypivalate, t-butyl peroxy-2-ethyl-hexanoate; di-(4-tert-butylcyclohexyl) peroxydicarbonate, 2,2'-azo-bis(isobutyronitrile), 2,2'-azo-bis(2,4-dimethylvaleronitrile), or 1,1'-azo-bis(cyanocyclohexane), and mixtures thereof.

14. A composition according to claim 1 wherein, if necessary, said reaction product is filtered to remove excess oil before addition of water thereto.

15. A composition according to claim 1 wherein said pharmaceutical medicament is a topically administered compound.

16. A composition according to claim 15 wherein said pharmaceutical medicament is metronidazole, diisopyramide phosphate, hydrocortisone, oxiconazole, ketoconazole, nystatin or erythromycin.

* * * * *